United States Patent [19]

Studeneer et al.

[11] 4,168,311

[45] Sep. 18, 1979

[54] HYDROXYQUINOLINE CARBAMATES AND N-OXIDE HYDROXYQUINOLINE CARBAMATES AND THEIR USE AS INSECTICIDES

[75] Inventors: Adolf Studeneer; Gerhard Salbeck, both of Kelkheim; Ludwig Emmel, Bergen-Enkheim; Werner Knauf, Eschborn, all of Fed. Rep. of Germany

[73] Assignee: Hoechst Aktiengesellschaft, Frankfurt am Main, Fed. Rep. of Germany

[21] Appl. No.: 808,368

[22] Filed: Jun. 20, 1977

Related U.S. Application Data

[63] Continuation-in-part of Ser. No. 531,172, Dec. 9, 1974, abandoned, and Ser. No. 592,801, Jul. 3, 1975, abandoned.

[30] Foreign Application Priority Data

Dec. 10, 1973 [DE] Fed. Rep. of Germany ....... 2361438
Jul. 6, 1974 [DE] Fed. Rep. of Germany ....... 2432635

[51] Int. Cl.$^2$ ............... A61K 31/47; C07D 215/22
[52] U.S. Cl. ................... 424/258; 546/153; 546/157; 546/110; 546/90
[58] Field of Search ............ 424/258; 260/287 L, 260/287 T

[56] References Cited

U.S. PATENT DOCUMENTS

| | | | |
|---|---|---|---|
| 3,005,823 | 10/1961 | Kaeding | 260/287 L |
| 3,362,960 | 1/1968 | Hodel | 424/258 |
| 3,384,538 | 5/1968 | Hodel | 424/258 |
| 3,538,099 | 11/1970 | Rohr et al. | 260/287 L |
| 3,793,314 | 2/1974 | Nardi et al. | 260/287 L |
| 3,818,012 | 6/1974 | Nikles | 260/287 T |

FOREIGN PATENT DOCUMENTS

1276516 6/1972 United Kingdom .

OTHER PUBLICATIONS

Elderfield, Chemistry of Quinoline, pp. 167–170, (1952).
Culvenor, Reviews, Pure and Applied Chem., vol. 3, 1953, pp. 83–88.

*Primary Examiner*—David Wheeler
*Attorney, Agent, or Firm*—Curtis, Morris & Safford

[57] ABSTRACT

Hydroxypyridine carbamates of the formula

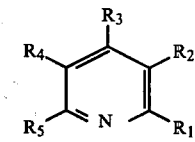

I wherein $R_1$ to $R_5$ as defined below are valuable insecticides and particularly aphicides and Compounds of the formula

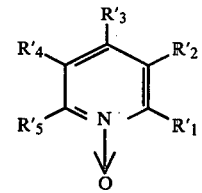

I' wherein one of $R'_1$ and/or $R'_3$ are substituted carbamoyl and the other is preferably hydrogen or methyl, $R'_2$ is a variety of substituents among which is hydrogen and acetyl, and $R'_3$ and $R'_4$ preferably form together a saturated or unsaturated $C_4$-chain which may be substituted, are valuable aphicides.

17 Claims, No Drawings

HYDROXYQUINOLINE CARBAMATES AND N-OXIDE HYDROXYQUINOLINE CARBAMATES AND THEIR USE AS INSECTICIDES

This application is a C.I.P. of, and combines, discloses and claims only subject matter disclosed in both applicants' pending application Ser. No. 531,172, filed Dec. 9, 1974, and Ser. No. 592,801, filed July 3, 1975, both now abandoned which applications claim priority to German application No. P 23 61 438.2, filed Dec. 10, 1973, and German application No. P 24 32 635.0, filed July 7, 1974, respectively and the aforesaid claims to priority are also made herein.

This invention provides new hydroxy pyridine carbamates of the general formula I

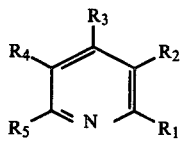

wherein
one of the radicals $R_1$ and $R_3$ represents a group of formula II

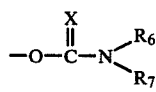

and the other represents hydrogen, $(C_1-C_6)$alkyl, halomethyl, $(C_1-C_6)$alkoxy, $(C_1-C_6)$alkylthio, $(C_1-C_4)$alkoxycarbonyl, di$(C_1-C_4)$alkylaminocarbonyl, phenyl, phenyl$(C_1-C_3)$alkyl, $(C_5-C_6)$cycloalkyl, halogen, cyano, phenoxy, phenylthio, $(C_1-C_4)$alkoxymethyl, mono- and di$(C_1-C_4)$alkylamino, N-pyrrolidino N-pyrrolidino or N-piperidino, $R_2$ represents hydrogen, $(C_1-C_6)$alkyl, $(C_2-C_6)$alkenyl, $(C_2-C_6)$alkinyl, $(C_1-C_3)$alkoxy or alkylthio, phenylthio, $(C_5-C_6)$cycloalkyl, phenyl$(C_1-C_3)$alkyl, $(C_1-C_3)$alkyl-carbonyl, $(C_1-C_6)$alkoxycarbonyl, benzoyl, di-$(C_1-C_6)$alkylaminomethyl, halogen, —CN, —NO$_2$, —NH$_2$, di$(C_1-C_3)$alkylaminocarbonyl, mono$(C_1-C_6)$alkylamino, di$(C_1-C_6)$alkylamino or $(C_1-C_4)$alkylcarbonylamino;

$R_1$ and $R_2$ together represent $(C_3-C_5)$alkylene or a radical of the formula —CH=CH—CH=CH—;

$R_4$ and $R_5$ are hydrogen, $(C_1-C_4)$alkyl, chlorosubstituted methyl, halogen, $(C_1-C_6)$alkoxycarbonyl or $(c_1-c_3)$alkylcarbonyl;

$R_4$ and $R_5$ together are a $(C_3-C_5)$alkylene radical or a radical of the formula CH=CH—CH=CH—, wherein one or two of the —CH= groups may be replaced by N= and which radicals may be substituted by halogen, $(C_1-C_{18})$alkyl, $(C_1-C_3)$alkoxy, $(C_1-C_3)$alkylthio, halogen$(C_1-C_2)$alcoxy, halogen$(C_1-C_2)$alkylthio, halomethyl, $(C_5-C_7)$cycloalkyl, phenoxy, phenylthio, NH$_2$, acetylamino, benzoylamino, phenylamino, di-$(C_1-C_4)$alkylamino, NO$_2$, CN, $(C_1-C_3)$alkylcarbonyl, mono-$(C_1-C_3)$alkylureido, di-$(C_1-C_3)$alkylureido, di$(C_1-C_3)$alkylformamidino, $C_1-C_3$)alkoxycarbonylmethoxy, $(C_1-C_6)$alkoxycrbonyl, di$(C_1-C_4)$alkylaminocarbonyl, benzthiazol-2-yl or a di-thiolane rest;

$R_4$ and $R_5$ together further represent a radical of formula

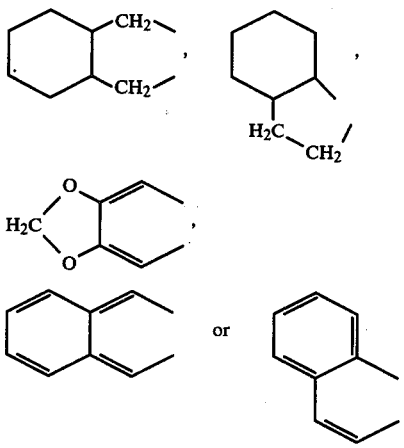

$R_6$ and $R_7$ are CH$_3$, C$_2$H$_5$, CH$_2$Cl, CH$_2$OCH$_3$ and CH$_2$SCH$_3$, and X is oxygen or sulphur.

Among the aforesaid radicals the following are preferred:
X=0
$R_6$ and $R_7$=CH$_3$
The group

is preferably in $R_3$-position. If $R_1$ or $R_3$ are not a group of formula II, they preferably are hydrogen $(C_1-C_3)$alkyl, Cl, CH$_2$Cl, CHCl$_2$, CCl$_3$, CF$_3$, $(C_1-c_4)$alkoxymethyl; especially preferred is $R_1$=hydrogen or $(C_1-C_3)$alkyl, and $R_2$=hydrogen, CN, F, COCH$_3$ or COOCH$_3$ $R_4$ and $R_5$ preferably are each hydrogen, CH$_3$, F or together form a $(C_3-C_5)$alkylene radical or the radical of the formula —CH=CH—CH=CH—. In the latter case derivatives of quinoline are obtained which themselves are either—preferably—non-substituted in the benzene nucleus or substituted by F, Cl, $(C_1-C_4)$alkyl, $(C_1-C_3)$alkoxy, $(C_1-C_3)$alkylthio, CN or methylenedioxy. In case $R_4$ and $R_5$ together form a $(C_3-C_5)$alkylene radical, derivatives of tetrahydroquinonline, trimethylene pyridine are pentamethylene pyridine are obtained; in these compounds the partially hydrated nucleus is also preferably -non-substituted or substituted by one of the radicals specified for quinoline derivatives, furthermore by CF$_3$or di$(C_1-C_2)$alkylamino.

The compounds described by formula I can be prepared from compounds of formula IIIa or IIIb, wherein either $R_1$ or $R_3$ is hydroxy:

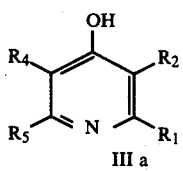
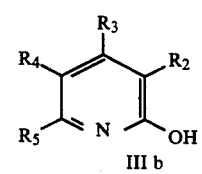

The compounds of formulae IIIa and IIIb may be present in the tautometric pyridone form:

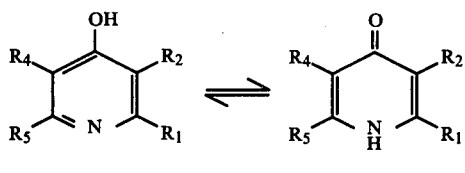

IIIa          IIIa'

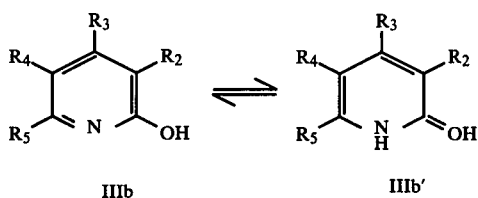

IIIb          IIIb'

In both cases so-called "ambient" anions are formed by the action of bases:

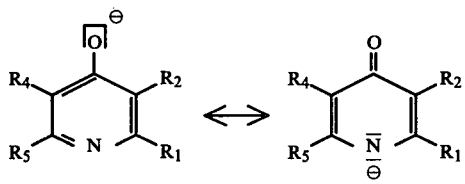

which react with alkylating or acylating agents, either at the O- or N-atom. By applying suitable reaction conditions, the reaction can be directed so as to produce the preferably or exclusively O-substituted products of formula I.

(1) In a preferred embodiment of the process according to the invention the compounds of formulae IIIa or IIIb are reacted with at least stoichiometric quantities of carbamoyl halides or thiocarbamoyl halides of formula IV

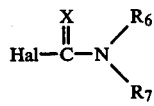          IV wherein Hal represents a halogen atom, especially chlorine or bromine.

It is especially preferable to use an excess of from 10-100% of the halide of formula IV. The reaction is carried out by dissolving or suspending the compounds of formulae IIIa or IIIb in an anhydrous inert solvent or diluent such as chloroform, an aliphatic ketone, acetonitrile or dimethyl formamide and adding an organic base such as triethylamine, pyridine, quinoline or an inorganic basic compound, e.g. sodium carbonate, potassium carbonate or calcium carbonate in at least stoichiometric quantities; subsequently, the N,N-dialkylcarbamoyl halide is added at temperatures between about 0° and 80° C.

So as to achieve the intended O-acylation of the ambident anions being formed upon addition of the base, polar solvents are used and the reaction temperature is advantageously kept as low as possible. Though reaction temperatures above 30° C. increase the reaction rate, in some cases the portion of N-acylated product increases with increasing temperature to the detriment of O-acylated products.

Reaction time varies depending on the base used and on the type of the substituents $R_1$ to $R_5$, but the reaction usually requires 4 to 12 hours.

(2) In another preferred embodiment of the process the compounds of formula IIIa and IIIb are reacted with phosgene, thiophosgene or chloroformic acid (thion)esters and the intermediate products thus obtained are further reacted with secondary amines of the formula

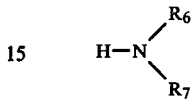

most conveniently in the presence of a solvent or of a suitable base.

The reaction conditions applied in this variation of the process are generaly known from similar reactions and are more extensively described in the Examples.

(3) Compounds of formula I wherein $R_1$ and/or $R_4$ and $R_5$ form a substituted or unsubstituted saturated alkylene chain, may be prepared from the correspondng unsaturated compounds by hydrogenation in known manner.

(4) If compounds of formula I are desired wherein $R_4$ and $R_5$ form an alkenyl cycle which is substituted by an amino group, these compounds may be prepared from the corresponding nitro compounds by means of catalytic hydrogenation.

The compounds of formula I are isolated from the reaction mixture according to processes (1) and (2) in known manner by filtering off the precipitated amine hydrohalides, alkali metal halides or alkali earth metal halides formed as by-products in the reaction and by concentrating the filtrate containing the reaction product. If a catalytic reduction is carried out according to processes 3 and 4, the catalyst is also eliminated by filtration.

For further purification the crude products may be distilled in vacuo if necessary, or they may be recrystalized from an organic solvent.

The compounds of formula I represent colorless to slightly yellowish crystalline solids or highly viscous liquids. They are well soluble in most of the organic solvents but only slightly soluble in water. The aqueous solutions are slightly basic.

The compounds of formula III which are used as initial compounds for the processes according to (1) and (2) can be prepared by processes known from literature or they may be prepared according to analogous processes.

The preparation of such initial compounds is described, for example, in the following publications:

U.S. Pat. No. 1.147.760; German Offenlegungsschrift (DOS) No. 2.058.002;

DOS No. 1.620.066; DOS 2.103.728;

Chem. Rev. 43, 43–68 (1948); J. Am. Chem. Soc. 68, 2685 (1946); 68, 2686 (1946); 69, 365 (1947); 69, 371 (1947); 69, 374 (1947);

Monatshefte für Chemie 100, 132–135 (1969);

The compounds of formula I according to the invention have a highly selective insecticidal activity which is directed almost exclusively against aphids, and furthermore possess excellent systemic properties. They show the same efficiency, whether absorbed via the plant foliage or via the root system. Therefore, aphids living hidden inside galls and other parts of the plants that are difficult to reach can also be combated with good results. They are furthermore active against aphids which have become resistant to phosphoric acid esters.

Examples of aphids which can be combated successfully by the new compounds are *Brevicoryne brassicae, Myzaphis rosarium, Aphis schneideri; Eriosomatidae* such as *Eriosoma lanigerum;* gall-forming aphids such as Pemphigus spec. as well as *Myzodes persicae.*

On the other hand, useful coleopters (such as lady bugs), butterflies, orthopterae, dipterae, hymenopterae (such as ichneumon flies), and predatory mites feeding on insect pests are not or only slightly affected even by high concentrations of the active ingredients. The action on aquatic organisms is insignificant; the compounds having an action on fish only at high concentrations.

The compounds of the present invention or the preparations containing them may be applied in widely varied manners. They may be applied to the foliage and/or affected parts of it or, on the other hand, to the earth surrounding the plant.

Marketable compositions containing these compounds may consist of dusting formulations, powders or granules, wherein the active ingredient is present as an admixture to solid extenders or carrier materials such as inert substances in powder or granular form. Generally, these compositions contain from 3–75% of these compounds. Suitable solid extenders or carrier materials are, for example, kaolin, bentonite, diatomaceous earth, dolomite, calcium carbonate, talcum, ground magnesia (chalk), fuller's earth, plaster or agrillaceous earth. The compositions may also be used as wettable powders which contain—in addition to the active ingredient—known wetting agents and/or dispersing agents and optionally fillers and/or emulsifiers as further additives.

For application in the field these formulations are further diluted with suitable solvents, preferably with water. The concentration of active ingredient in such ready-to-use formulations may vary within wide limits depending on the mode of application (foliar or root), the type of aphid being combatted etc. Generally, the concentration may be between about 0.0002 and 1% active substance.

The compositions may also be present as liquid preparations as concentrated emulsions for spray liquors which normally contain the active ingredient together with one or several wetting agents, dispersing auxiliaries or emulsifiers. For liquid preparations organic solvents may also be used.

The wettable, dispersing and emulsifying agents may be of either one of the cationic, anionic or non-ionic type.

The compounds of formula I may also be used as active ingredients in fumigants.

The following examples illustrate the invention in detail without—at that—limiting the range of the invention:

EXAMPLES OF PREPARATION

EXAMPLE 1

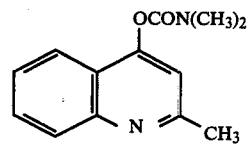

2-methyl-4-dimethylaminocarbonyloxyquinoline (a) To a suspension of 75 g (0.47 mole) of 2-methyl-4-hydroxyquinoline in approximately one liter of acetonitrile 130 g of anhydrous potassium carbonate were added at room temperature. The mixture was heated to reflux temperature ($\sim 80°$ C.) while stirring vigorously for about two hours. After cooling to room temperature, 76.7 g (0.71 mole) of dimethylcarbamic acid chloride were added and the reaction mixture was stirred vigorously at room temperature for about 8 hours. After cooling, it was being suction-filtered, the filter cake was washed additionally with some acetonitrile. The filtrates were combined and the acetonitrile was eliminated by water jet vacuum.

The residual oil was submitted to fractionation in vacuo. At a temperature from 158°–161° C. (0.05 mm) the distillation yielded 100 g of a colorless highly viscous liquid, the elementary analysis values of which corresponded to those obtained for 2-methyl-4-(dimethylaminocarbonyloxy)quinoline; when submitting this liquid to thin-layer chromatography and to NMR spectrum, it proved to be uniform. Besides the results of the NMR spectrum, the presence of a carbamate was further confirmed by IR spectroscopy.

(b) 24 g (0,15 mole) of 2-methyl-4-hydroxyquinoline were dissolved in 200 ml of dimethylformamide (anhydrous and free from amine), 23 g (0,22 mole) of triethylmine were added and, subsequently, 24 g (0,22 mole) of dimethylcarbamic acid chloride added dropwise.

The reaction mixture was heated to 60° C. (for about 8 hours) until thin-layer chromatography showed the absence of starting material.

Separated aminohydrochloride was suctioned off, the reaction mixture was cooled to 0° to 10° C. The filter cake was washed with a minor quantity of cold dimethyl-formamide, the filtrates were combined and the solvent was eliminated in vacuo. The oil residue was submitted to fractional distillation.

At 145° C. (0,01 mm) 21 g of a colorless and highly viscous liquid were obtained.

EXAMPLE 2

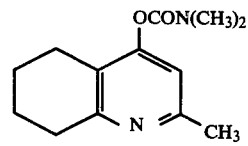

2-methyl-4-dimethylaminocarbonyloxy-5,6,7,8-tetrahydroquinoline (a) 287 g (1,76 mole) of 2-methyl-4-hydroxy-5,6,7,8-tetrahydro-quinoline were dissolved in 1650 ml of chloroform (anhydrous and free from alcohol); to this solution 267 g (2,64 mole) of triethylamine and 284,5 g (2,63 mole) of dimethylcarbamic acid chloride were added successively.

The mixture is then heated at an interior temperature of 50° C. until after approximately 6 hours thin-layer chromatography did not show any initial compound.

After cooling to room temperature, about one liter of ice water was added dropwise to the reaction mixture while stirring, until the aminohydrochloride formed in the reaction was dissolved and two liquid phases were obtained. The organic phase was separated, washed with a minor quantity of water, dried and concentrated. At a bath temperature of 100° C. and approximately 2–3 mm of pressure some ml of an oily by-product distilled off. The remaining oily residue was dissolved in boiling n-hexane.

347 g of a colorless product having a melting point from 89°–90° C. crystallized out of the cooled solution. On thin-layer chromatography this product proved to be uniform and elementary analysis yielded the expected values for 2-methyl-4-dimethylaminocarbonyloxy-5,6,7,8-tetrahydroquinoline. IR spectrographic and NMR spectrographic data confirmed the formulation of the expected O-acylation product.

(b) 16,3 g (0,1 mole) of 2-methyl-4-hydroxy-5,6,7,8-tetrahydroquinoline were dissolved in 150 ml of chloroform (anhydrous and free from alcohol) and this solution was added dropwise to a previously prepared solution of approximately 20 g (0,2 mole) of phosgene in 100 ml of chloroform at a maximum temperature of +10° C. After a period of two hours at +10° C., the reaction was completed at room temperature for another hour. Non-reacted phosgene was then blown out of the solution by means of a dry nitrogen current and the solvent was eliminated in vacuo at room temperature. The semisolid residue was again dissolved in dry chloroform free from alcohol, the solution was cooled to +10° C. and an excess quantity of dimethylamine was introduced at this temperature. After standing for two days at room temperature, chloroform and excess amine was eliminated by distillation in vacuo. The residue was digested with ice water, separated from water and dissolved in toluene. After drying and evaporating the toluene a residue of 7 g was obtained which crystallized thoroughly when being submitted to trituration with n-hexane. Recrystallization from n-hexane yielded 4 g of a uniformly crystalline product having a melting point of from 83°–89° C. This product proved to be identical with the product obtained according to example(2a).

(c) 5 g of a nickel catalyst consisting of, 50 percent by weight of finely distributed nickel on diatomaceous earth were added to a solution of 20 g of the substance according to example (1) in 1 liter of toluene and the whole was heated at 100° C. in a 2 l steel autoclave with hydrogen at a pressure of 100 atmospheres. After 20 hours the batch was cooled, the catalyst filtered off, washed with toluene and the filtrates were concentrated. The residue was distilled, 11 g of a product (b.p.$_{0.1}$130°–142° C.) were obtained. On crystallization this product proved to be identical with the product obtained according to example 2a).

EXAMPLE 3

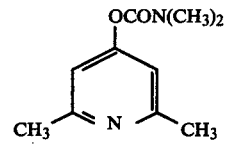

2,6-dimethyl-4-dimethylaminocarbonyloxy-pyridine 30,8 g (0,25 mole) of 2,6-dimethyl-4-hydroxypyridine were suspended in 500 ml of acetonitrile, 69 g (0,5 mole) of potassium carbonate were added and the mixture was heated to reflux temperature for 2 hours. Subsequently 47 g (0,44 mole) of dimethylcarbamic acid chloride were added at an interior temperature of approximately 60°–70° C. and the mixture was maintained for two hours at about 80° C.

After cooling the liquid phase was suctioned off, the residue was washed with acetonitrile and the combined solutions were concentrated (finally in vacuo). The viscous residue was dissolved in hot n-hexane. On cooling 37 g of colorless, uniform (DC) 2,6-dimethyl-4-dimethylaminocarbonyloxypyridine having a melting point of from 75°–76° C. were obtained. Chemical structure as well as composition were confirmed by elementary analysis, IR and NMR spectrography.

The following table shows a number of additional compounds prepared according to example 1.

TABLE

| example number | formula | base solvent | reaction temperature (°C.) reaction period (hours) | melting point °C. (solvent) boiling point °C. (mm Hg) |
| --- | --- | --- | --- | --- |
| 4 | ![quinoline-OCON(CH3)2] OCON(CH$_3$)$_2$ | K$_2$CO$_3$ CH$_3$CN | 80 2 | 47° C. (cyclohexane) 132° C. (0.01) |
| 5 | ![quinoline-OCON(C2H3)2] OCON(C$_2$H$_3$)$_2$ | K$_2$CO$_3$ CH$_3$CN | 80 6.5 | 54°–55° C. (n-hexane) 167°–170° C. (0.05) |

TABLE -continued

| example number | formula | base solvent | reaction temperature (°C.) reaction period (hours) | melting point °C. (solvent) boiling point °C. (mm Hg) |
|---|---|---|---|---|
| 6 | 4-OCON(CH$_3$)$_2$, 3-CH$_3$, 2-CH$_3$ quinoline | K$_2$CO$_3$ CH$_3$CN | 80 / 4 | 98°–99° C. (n-hexane) |
| 7 | 4-OCON(C$_2$H$_5$)$_2$, 2-CH$_3$, 5,6,7,8-tetrahydroquinoline | K$_2$CO$_3$ CH$_3$CN | 80 / 9 | 139° C. (0.01) |
| 8 | 4-OCON(CH$_3$)$_2$, 2-CH$_3$, 8-CH$_3$ quinoline | (C$_2$H$_5$)$_3$N DMF | 25 / 65 | 64°–65° C. (n-hexane) |
| 9 | 4-OCON(CH$_3$)$_2$, 2-CH$_3$, 8-CH$_3$, 5,6,7,8-tetrahydroquinoline | (C$_2$H$_5$)$_3$N CHCl$_3$ | 25 / 65 | 134°–136° C. (0.005) |
| 10 | 4-OCON(CH$_3$)$_2$, 6-CH$_3$, 2-CH$_3$ quinoline | K$_2$CO$_3$ CH$_3$CN | 80 / 7 | 91°–92° C. (n-hexane) |
| 11 | 4-OCON(CH$_3$)$_2$, 6-CH$_3$, 8-CH$_3$, 2-CH$_3$ quinoline | K$_2$CO$_3$ CH$_3$CN | 80 / 4 | 93°–94° C. (n-hexane) |
| 12 | 5-CH$_3$, 4-OCON(CH$_3$)$_2$, 8-CH$_3$, 2-CH$_3$, 5,6,7,8-tetrahydroquinoline | K$_2$CO$_3$ CH$_3$CN | 80 / 6 | 147° C. (0.001) |
| 13 | 6-CH(CH$_3$)$_2$, 4-OCON(CH$_3$)$_2$, 2-CH$_3$ quinoline | (C$_2$H$_5$)$_3$N CHCl$_3$ | 60 / 6 | 69°–70° C. (n-hexane) |
| 14 | 6-CH(CH$_3$)$_2$, 4-OCON(CH$_3$)$_2$, 2-CH$_3$, 5,6,7,8-tetrahydroquinoline | (C$_2$H$_5$)$_3$N CHCl$_3$ | 50 / 4 | 62°–63° C. (n-hexane) |

TABLE -continued

| example number | formula | base solvent | reaction temperature (°C.) reaction period (hours) | melting point °C. (solvent) boiling point °C. (mm Hg) |
|---|---|---|---|---|
| 15 | 8-isopropyl-4-(N,N-dimethylcarbamoyloxy)-2-methylquinoline | $K_2CO_3$ CH$_3$CN | 80 6 | 99°–100° C. (n-hexane) |
| 16 | 8-isopropyl-4-(N,N-dimethylcarbamoyloxy)-2-methyl-5,6,7,8,8a,-hexahydroquinoline | $K_2CO_3$ CH$_3$CN | 80 6 | 69° C. (n-hexane) 139°–140° C. (0.01) |
| 17 | 6-tert-butyl-4-(N,N-dimethylcarbamoyloxy)-2-methylquinoline | $K_2CO_3$ CH$_3$CN | 80 6 | 63° C. (n-hexane) |
| 18 | 6-tert-butyl-4-(N,N-dimethylcarbamoyloxy)-2-methyl-5,6,7,8-tetrahydroquinoline | $K_2CO_3$ CH$_3$CN | 80 6 | 166° C. (0.03) |
| 19 | 6-cyclohexyl-4-(N,N-dimethylcarbamoyloxy)-2-methyl-5,6,7,8-tetrahydroquinoline | $K_2CO_3$ CH$_3$CN | 80 7.25 | 96°–97° C. (n-hexane) |
| 20 | 7-trifluoromethyl-4-(N,N-dimethylcarbamoyloxy)-2-methyl-5,6,7,8-tetrahydroquinoline | $(C_2H_5)_3N$ DMF | 70 65 | 74°–75° C. (n-hexane) |
| 21 | 6-fluoro-4-(N,N-dimethylcarbamoyloxy)-2-methylquinoline | $(C_2H_5)_3N$ DMF | 60–70 18.5 | 79°–80° C. (n-hexane) |
| 22 | 6-fluoro-4-(N,N-dimethylcarbamoyloxy)-2,3-dimethylquinoline | $K_2CO_3$ CH$_3$CN | 80 6 | 140° C. (acetonitrile) |
| 23 | 6-chloro-4-(N,N-dimethylcarbamoyloxy)-2-methylquinoline | $K_2CO_3$ CH$_3$CN | 80 5 | 140°–105° C. (n-hexane) |

TABLE -continued

| example number | formula | base solvent | reaction temperature (°C.) reaction period (hours) | melting point °C. (solvent) boiling point °C. (mm Hg) |
|---|---|---|---|---|
| 24 | 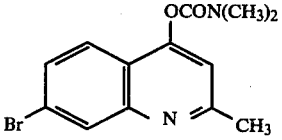 | K$_2$CO$_3$ CH$_3$CN | 80 2 | 151°–152° C. (Toluene) |
| 25 | 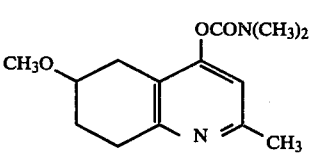 | (C$_2$H$_3$)$_3$N CHCl$_3$ | 80 4 | 49°–51° C. (n-hexane) |
| 26 | 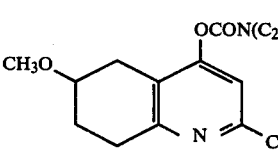 | K$_2$CO$_3$ CH$_3$CN | 80 6.5 | 160°–163° C. (0.01) |
| 27 | 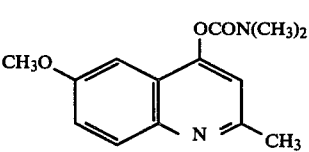 | (C$_2$H$_3$)$_3$N DMF | 90 65 | 80°–81° C. (n-hexane) |
| 28 | 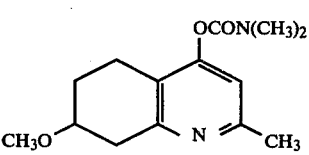 | (C$_2$H$_3$)$_3$N DMF | 70 8 | 170°–173° C. (0.01) |
| 29 | 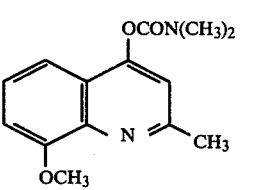 | K$_2$CO$_3$ CH$_3$CN | 80 10 | 106°–107° C. (n-hexane/ toluene) |
| 30 | 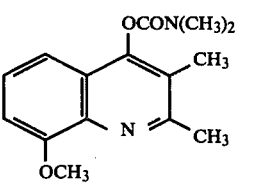 | K$_2$CO$_3$ CH$_3$CN | 80 18 | 168°–170° C. (n-hexane/ toluene) |
| 31 | 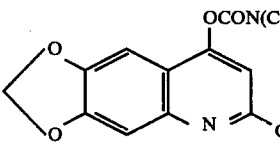 | (C$_2$H$_5$)$_3$N DMF | 40–50 70 | 154°–155° C. (n-hexane/ toluene) |
| 32 | 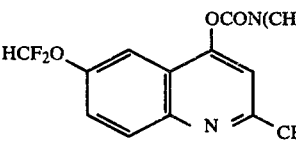 | (C$_2$H$_5$)$_3$N DMF | 70 10 | 112°–113° C. (cyclohexane) |

TABLE -continued

| example number | formula | base solvent | reaction temperature (°C.) reaction period (hours) | melting point °C. (solvent) boiling point °C. (mm Hg) |
|---|---|---|---|---|
| 33 | 7-cyclohexyl-4-OCON(CH₃)₂-2-methylquinoline | K₂CO₃ CH₃CN | 80 5 | 192°–193° C. (0,05) |
| 34 | 6-C₆H₅O-4-OCON(CH₃)₂-2-methylquinoline | K₂CO₃ CH₃CN | 30 1,5 | 107°–108° C. (n-hexane) |
| 35 | 8-OC₆H₅-4-OCON(CH₃)₂-2-methylquinoline | K₂CO₃ CH₃CN | 80 7,5 | 126°–127° C. (n-hexane) |
| 36 | 7-C₂H₅S-4-OCON(CH₃)₂-2-methylquinoline | (C₂H₅)₃N DMF | 60–70 19 | 58°–59° C. (n-hexane) 226°–228° C. (0,01) |
| 37 | 6-(C₂H₅)₂N-4-OCON(CH₃)₂-2-methyl-octahydroquinoline | (C₂H₅)₃N CH₃CN | 75 8 | 66°–67° C. (n-hexane) |
| 38 | 6-O₂N-4-OCON(CH₃)₂-quinoline | K₂CO₃ CH₃CN | 60 2 | 153° C. (acetonitrile) |
| 39 | 6-H₂N-4-OCON(CH₃)₂-quinoline | Hydrieren Toluol | 100 5 | 130°–131° C. (toluene) |
| 40 | OCON(CH₃)₂ substituted methyl-octahydrophenanthridine | K₂CO₃ CH₃CN | 80 6 | 78°–79° C. (n-hexane) |
| 41 | 4-OCON(CH₃)₂-2-methylbenzo[h]quinoline | K₂CO₃ CH₃CN | 80 7 | 129°–130° C. (n-hexane) |

TABLE -continued

| example number | formula | base solvent | reaction temperature (°C.) reaction period (hours) | melting point °C. (solvent) boiling point °C. (mm Hg) |
|---|---|---|---|---|
| 42 | 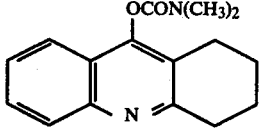 | K₂CO₃ CH₃CN | 80 6 | 116°–117° C. (cyclohexane) |
| 43 | 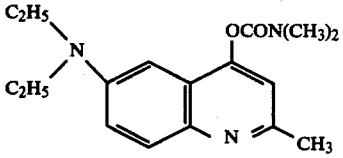 | (C₂H₅)₃N CHCl₃ | 23 110 | 192°–193° C. (0.05) |
| 44 | 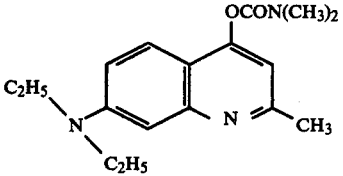 | (C₂H₅)₃N CHCl₃ | 60 11 | 207° C. (0.05) |
| 45 | 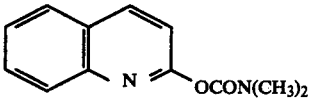 | K₂CO₃ CH₃CN | 80 8 | 130°–131° C. (n-hexane/ toluene) |
| 46 | 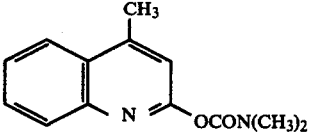 | K₂CO₃ CH₃CN | 80 3 | 68°–69° C. (n-hexane/ toluene) |
| 47 | 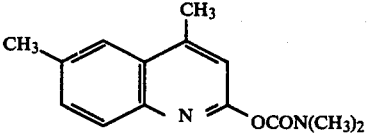 | K₂CO₃ CH₃CN | 80 3 | 91°–92° C. (n-hexane/ toluene) |
| 48 | 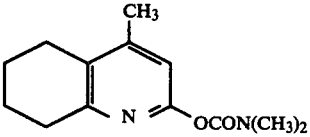 | (C₂H₅)₃N CHCl₃ | 50 9 | 151°–153° C. (0.1) |
| 49 | 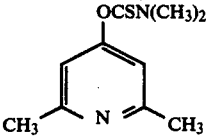 | K₂CO₃ CH₃CN | 25 48 | 82°–83° C. (n-hexane) |
| 50 | 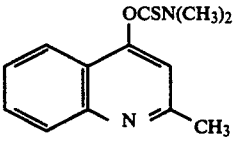 | K₂CO₃ CH₃CN | 25 8 | 93°–94° C. (n-hexane) |
| 51 | 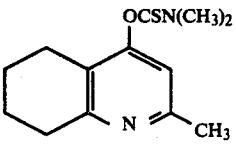 | K₂CO₃ CH₃CN | 80 36 | 60° C. (n-hexane) 162° C. (0.1) |

TABLE -continued

| example number | formula | base solvent | reaction temperature (°C.) reaction period (hours) | melting point °C. (solvent) boiling point °C. (mm Hg) |
|---|---|---|---|---|
| 52 | 4-OCON(CH$_3$)$_2$, 2-COOC$_2$H$_5$ quinoline | K$_2$CO$_3$ CH$_3$CN | 80 6 | 111° C. (n-hexane/ toluene) |
| 53 | 4-OCON(CH$_3$)$_2$, 3-NO$_2$ quinoline | K$_2$CO$_3$ CH$_3$CN | 25 3,5 | 102° C. (n-hexane) |
| 54 | 4-OCON(CH$_3$)$_2$, 3-COOC$_2$H$_5$ quinoline | K$_2$CO$_3$ CH$_3$CN | 25 48 | 71° C. (n-hexane) 193° C. (0.005) |
| 55 | 4-OCON(CH$_3$)$_2$, 3-CN quinoline | K$_2$CO$_3$ CH$_3$CN | 25 27 | 121° C. (n-hexane) |
| 56 | 4-OCON(CH$_3$)$_2$ 1,8-naphthyridine | K$_2$CO$_3$ CH$_3$CN | 80 7 | 93°–94° C. (n-hexane) |
| 57 | 4-OCON(C$_2$H$_5$)$_2$, 2,6-dimethylpyridine | K$_2$CO$_3$ CH$_3$CN | 60–80 16 | 100°–103° C. (0.01) |
| 58 | 4-OCON(CH$_3$)$_2$, 3-COOCH$_3$, 2,6-dimethylpyridine | (C$_2$H$_5$)$_3$N DMF | 60 4 | 149° C. (0.05) |
| 59 | 4-OCON(CH$_3$)$_2$, 3-COOC$_2$H$_5$, 2,6-dimethylpyridine | (C$_2$H$_5$)$_3$N CH$_3$CN | 80 12 | 141° C. (0.01) |
| 60 | 4-OCON(CH$_3$)$_2$, 3-COOCH$_3$, 2,6-dimethylpyridine | (C$_2$H$_5$)$_3$N DMF | 70 60 | 131°–141° C. (0.05) |
| 61 | 4-OCON(CH$_3$)$_2$, 3-COOCH$_3$, 5-Cl, 2,6-dimethylpyridine | (C$_2$H$_5$)$_3$N DMF | 70 40 | 125° C. (0.01) |

TABLE -continued

| example number | formula | base solvent | reaction temperature (°C.) reaction period (hours) | melting point °C. (solvent) boiling point °C. (mm Hg) |
|---|---|---|---|---|
| 62 | Br-substituted pyridine with OCON(CH$_3$)$_2$, COCH$_3$, and two CH$_3$ groups | (C$_2$H$_5$)$_3$N DMF | 25 48 | 100°–101° C. (ethanol) |
| 63 | 6-methyl-tetrahydroquinoline with 4-OCON(CH$_3$)$_2$ and 2-CH$_3$ | K$_2$CO$_3$ CH$_3$CN | 80 6 | 57° C. (n-hexane) 135° C. (0.01) |
| 64 | 6-(H$_3$CO-CO-)quinoline with 4-O-CO-N(CH$_3$)$_2$ and 2-CH$_3$ | triethyl-amine DMF | 40 5 | 95°–98° C. |
| 65 | 6-acetyl quinoline with 4-O-CO-N(CH$_3$)$_2$ and 2-CH$_3$ | K$_2$CO$_3$ acetonitrile | 40 48 | 123°–126° C. |
| 66 | quinoline with 4-O-CO-N(CH$_3$)$_2$ and 2-C$_2$H$_5$ | K$_2$CO$_3$ acetonitrile | 30 6 | 88°–92° C. |
| 67 | quinoline with 4-O-CO-N(CH$_3$)$_2$ and 2-C$_3$H$_7$n | K$_2$CO$_3$ acetonitrile | 40 10 | 176°–180° C. (0.2) |
| 68 | 5,6,7,8-tetrahydroquinoline with 4-O-CO-N(CH$_3$)$_2$ and 2-C$_3$H$_7$-n | K$_2$CO$_3$ DMF | 80 1 | 170°–175° C. (0.05 mm) |
| 69 | 6-methoxyquinoline with 4-O-CO-N(CH$_3$)$_2$ and 2-C$_3$H$_7$-n | K$_2$CO$_3$ DMF | 90 1 | 40°–44° C. |

TABLE -continued
| example number | formula | base solvent | reaction temperature (°C.) reaction period (hours) | melting point °C. (solvent) boiling point °C. (mm Hg) |
|---|---|---|---|---|
| 70 | ![structure] H3CO, H, N, C5H7-n, O-C-N(CH3)2 | K2CO3 DMF | 80 1 | 180°-190° C. (0.2 mm) |
In the same way the following compounds can be prepared:
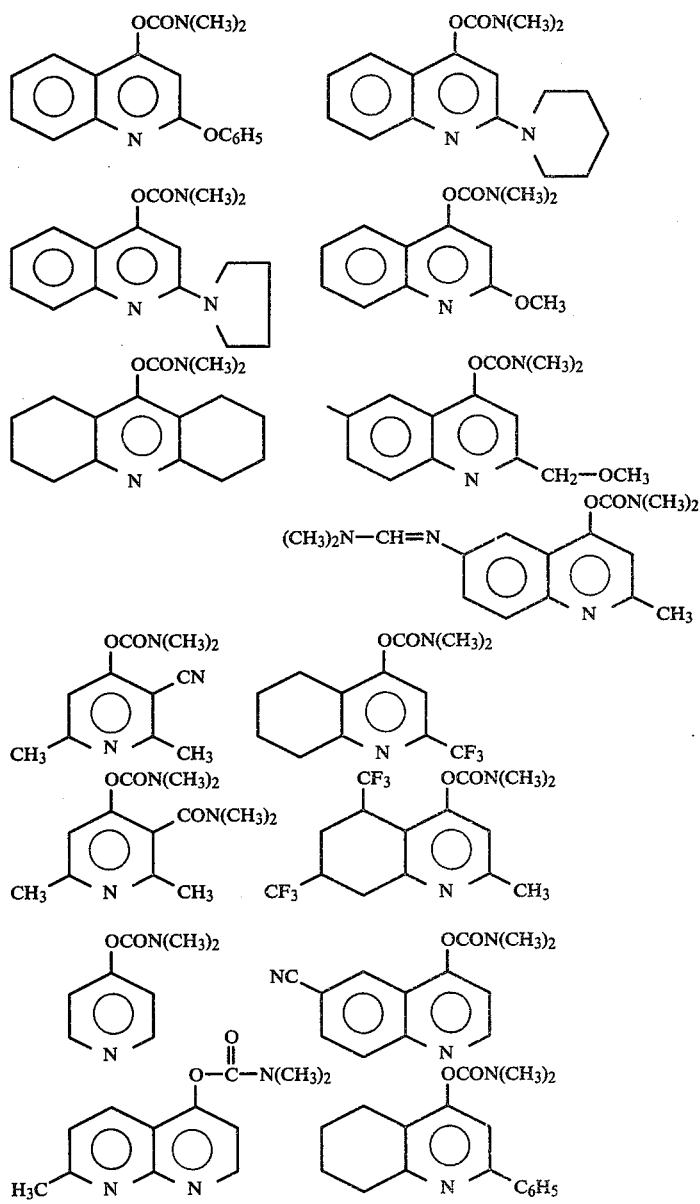

-continued

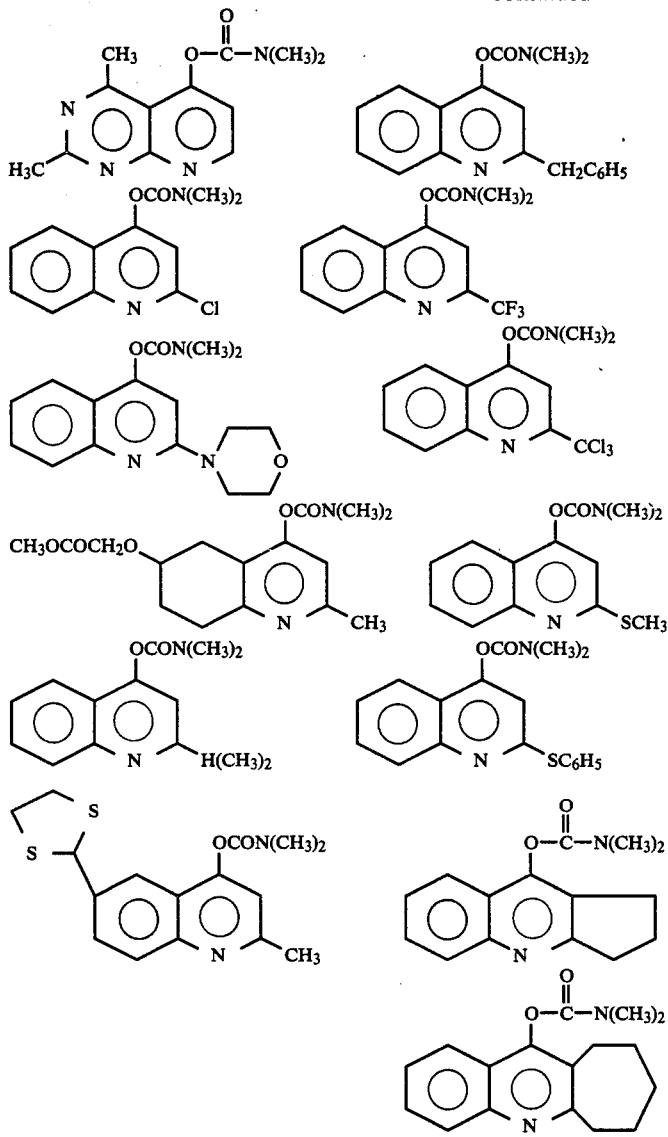

FORMULATION EXAMPLES

Example A

A wettable powder easily dispersable in water is obtained by grinding together

| | |
|---|---|
| 12 g | of 2-methyl-4-(dimethylaminocarbonyloxy)-quinoline as active ingredient and |
| 3 g | of Silcasil(R)* (highly dispersed synthetic silicic acid), and blending this with |
| 45–43 g | of a pre-mix consisting of |
| 10 g | of cellulose pitch (potassium salt of ligninsulfonic acid) |
| 49 g | of Ca-Mg-Al-silicate |
| 11.5 g | of highly dispersed synthetic silicic acid |
| 3.5 g | of polypropylene glycol (m.w. 750) |
| 1 g | of Na-oleylmethyltauride |
| 75 g | of preliminary blend |

That means that 60 g of this wettable powder contain
20 weight % of active ingredient
49 weight % of Ca-Mg-Al-silicate
16.5 wt. % of highly dispersed synthetic silicic acid
3.5 wt. % of polypropylene glycol (m.w. 750)
1 weight % of Na-oleylmethyltauride
10 weight % of cellulose pitch

Example B

An emulsifiable concentrate consists of:
1.5 g (15%) of 2-methyl-4-dimethylaminocarbonyloxy-5,6,7,8-tetrahydroquinoline
6.5 g (65%) of cyclohexane as solvent and
2.0 g (20%) of ethoxylated nonylphenol (nonyl (ethoxy)$_{10}$ phenol) as emulsifier.

BIOLOGICAL EXAMPLES

Example I

Potted horse beans (*Vicia faba*) were infested with 200 specimens each of bean aphids (*Doralis fabae*) and, after stabilization of the population, sprayed to the drip-off with decreasing concentrations of an aqueous dilution of the emulsion concentrate containing the compound described in example (1) as active ingredient 3 days later the percentage of killed aphids was determined by counting the numbers of surviving and dead insects.

The following table shows the mortality rate depending on the concentration of active substance (AS) in the aqueous dilution, as compared to the efficiency of two compounds having similar structures or comparable degrees of efficiency.

TABLE I

| structural formula | concentration of AS in the spray liquor in % | % of mortality |
|---|---|---|
| Compound of Example (1) (according to the invention | 0.00019 | 100 |
|  | 0.000095 | 98 |
|  | 0.000048 | 80 |
|  | 0.000024 | 50 |
| [quinoline-OCON(CH$_3$)$_2$ structure] Dutch Offenlegungsschrift No. 6.606.695 (comp. agent I) | 0.006 | 100 |
|  | 0.003 | 98 |
|  | 0.0015 | 60 |
|  | 0.0006 | 20 |
| Isolan (comp. agent II) | 0.005 | 100 |
|  | 0.0025 | 96 |
|  | 0.0012 | 60 |
|  | 0.0006 | 20 |

Similar or identical results were obtained with the compounds of examples 2, 3, 4, 5, 8, 9, 10, 11, 12, 14, 20, 21, 25, 28, 40, 46, 48, 60 and 63.

EXAMPLE II

Potted horse beans (*Vicia faba*), the root system of which was wrapped in sheet plastic, were infested with bean aphids (*Doralis fabae*) and treated with gradually decreasing concentrations of the product of example (60) in such a way that an aqueous dilution of a emulsion concentrate was uniformly distributed in the root area by means of a glass funnel. 8 days later the percentage of killed aphids was determined by counting the numbers of surviving and dead insects.

| mg of AS per root system | 0.5 | 0.25 | 0.125 | 0.06 | 0.03 |
|---|---|---|---|---|---|
| % of mortality | 100 | 100 | 94 | 81 | 40 |

Similar or identical data were obtained with the rest of the compounds specified in example (I).

EXAMPLE III

The stem of a horse bean plant about 25 cms high was wrapped in cotton (wadding) and covered with cellophane. By means of an injection syringe 2 ml of an aqueous suspension of wettable powder of the compound of example (1) having the specified concentration of active substance was uniformly distributed in the cotton pad. At the accordingly administered quantities of active substance bean aphids living on the leaves of the plant were destroyed as follows after 3 days:

| concentration of AS in the spray liquor in % | 0.25 | 0.125 | 0.06 | 0.03 | 0.015 |
|---|---|---|---|---|---|
| % of mortality | 100 | 100 | 86 | ~70 | <20 |

This test shows the capacity of the active substance to penetrate into plant tissue and to circulate within the plant. This same capacity is also characteristic for the other compounds specified in example I.

EXAMPLE IV

The compounds according to the present claims in the gaseous phase were also efficient against aphids (*Doralis fabae*).

When a potted plant infested with bean aphids was placed under a glass bell having a volume of 23 l and a filter paper of 133 cm$^2$ surface and containing a given quantity of active substance was suspended in the air-filled volume, the aphids on the test plant were destroyed after 2 days. A test carried out with the compound of example (3), gave the following results:

| mg of AS on the filter | 0.25 | 0.125 | 0.06 | 0.03 | 0.015 |
|---|---|---|---|---|---|
| % of mortality | 100 | 100 | 100 | 97 | 84 |

The other compositions specified in example I gave similar or identical results.

EXAMPLE V

Useful insects such as ichneumon flies (*Coccygomimus turionellae* (L.)) are not affected by concentrations effective against aphids. This is shown in the following experiment:

Rectangular-shaped filter papers (150 cm$^2$) are sprinkled uniformly by means of a pipet with acetone solutions of active substance in decreasing concentrations. After drying the filter paper is put inside a glass tube in such a way that its total interior wall surface is covered by the filter paper. Subsequently, 10 females of ichneumon flies are inserted in each of the glass tubes thus prepared and, after closing the tubes with a pierced cork, a constant flow of air (10 l of air per hour) is passed through (suppressing a possible gaseous phase, imitation of natural flow of air outdoors). The following mortality rates are found after 24 hours for the use of the compounds of example (1).

|  | mg of AS on the filter | % of mortality |
|---|---|---|
| Compound of example (1) | 0.012 | 100 |
|  | 0.006 | 40 |
| (as per the invention) | 0.003 | 0 |
|  | 0.0012 | 0 |
|  | 0.0006 | 0 |
|  | 0.0006 | 100 |
|  | 0.0003 | 100 |
| Carbaryl | 0.00015 | 40 |
| (compar. agent III) | 0.000075 | 0 |
| Isolan | 0.003 | 100 |
| (compar. agent II) | 0.0012 | 80 |
|  | 0.0006 | 0 |

The compositions mentioned in example I gave results similarly or equally favorable as those of example (1).

EXAMPLE VI

No action was observed on lady bugs (Coccinellidae) essentially feeding on aphids when the same concentration rates were used as those for combating aphids. The following example confirms this with respect to Imagines of the species *Coccinella septempunctata:*

On Petri dishes lined with filter paper 10 insects each of the above mentioned species were placed and then sprayed with decreasing concentrations of an aqueous dilution of the emulsion concentrate of the compound of example (1) (corresponding to 600 l/ha). The following mortality rates were found after 24 hours:

| mg of AS on the filter | % of mortality |
|---|---|
| 0.003 | 10 |
| 0.0015 | 0 |
| 0.0006 | 0 |
| 0.0003 | 0 |
| 0.00015 | 0 |

This invention also relates to compounds of the formula I′

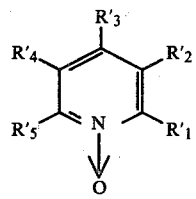

in which
one of the radicals $R_1$ or $R_3$ represents a radical of the formula II′.

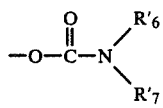

and the other is hydrogen, $(C_1-C_3)$alkyl, mono-, di-, or trichloromethyl, trifluoromethyl, $(C_1-C_3)$alkoxy, $(C_1-C_4)$alkoxycarbonyl, di$(C_1-C_4)$alkylaminocarbonyl, phenyl, phenyl$(C_1-C_3)$alkyl, $(C_5-C_6)$cycloalkyl, or halogen;
$R_2'$ is hydrogen, $(C_1-C_6)$alkyl, $(C_1-C_3)$alkoxy, $(C_5-C_6)$cycloalkyl, phenyl$(C_1-C_3)$alkyl, $(C_1-C_3)$alkylcarbonyl, $(C_1-C_6)$alkoxycarbonyl, benzoyl, halogen, nitro, di$(C_1-C_3)$alkylaminocarbonyl, $(C_1-C_4)$alkylcarbonylamino, or cyano,
$R_1'$ and $R_2'$ together are $(C_3-C_5)$alkylene or a radical of the formula

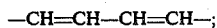

$R_4'$ and $R_5'$ are hydrogen, $(C_1-C_4)$alkyl, triflouromethyl, halogen, $(C_1-C_6)$alkoxycarbonyl, or $(C_1-C_3)$alkylcarbonyl;
$R_4'$ and $R_5'$ together are $(C_3-C_5)$alkylene or a radical of the formula

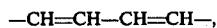

these radicals optionally being substituted by halogen, $(C_1-C_4)$alkyl, $(C_1-C_3)$alkoxy, halo$(C_1-C_2)$alkoxy, trifluoromethyl, phenoxy, acetylamino, benzoylamino, nitro, $(C_1-C_3)$alkylcarbonyl, mono- or di$(C_1-C_3)$alkylureido, $(C_1-C_3)$alkoxycarbonylmethoxy, or di$(C_1-C_4)$alkoxyaminocarbonyl; or $R_4'$ and $R_5'$ together are a radical of the formula

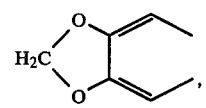

and $R_6'$ and $R_7'$ are $CH_3$, $C_2H_5$, $CH_2Cl$, or $CH_2OCH_3$.

Preferably one of the radicals $R_1'$ and $R_3'$ represents dimethylaminocarbonyl and the other one is methyl or hydrogen. $R_2'$ preferably stands for hydrogen, acetyl, $(C_1-C_2)$alkoxycarbonyl, or cyano, while $R_4'$ and $R_5'$ together are preferably tetramethylene or —CH═CH—CH═CH—, which are preferably unsubstituted or substituted by fluorine, chlorine, $(C_1-C_4)$alkyl, $(C_1-C_3)$alkoxy, or $CF_3$.

This invention also relates to a process for the manufacture of compounds of formula I′, which comprises oxidizing compounds of formulla III′

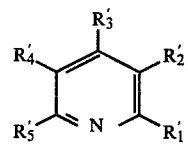

in known manner.

Suitable oxidizing agents are, besides hydrogen peroxide, peracids, for example performic acid, peracetic acid, halogenated peracetic acids such a petrifluoroacetic acid, perpropionic acid, perlactic acid, monopermaleic acid, monopersuccinic acid, perbenzoic acid, substituted perbenzoic acids such as 3-chloroperbenzoic acid, monoperphthalic acid, diperphthalic acid, percamphoric acid, or mixtures thereof. Performic acid, peracetic acid, monpermaleic acid, perbenzoic acid, monoperphthalic acid, 3-chloroperbenzoic acid and hydrogen peroxide are preferred.

If available, the aforesaid peracids can be used as such, or they can be prepared in situ, for example by reacting an excess of the basic carboxylic acid or the anhydride thereof with hydrogen peroxide, the excess of the carboxylic acid or the anhydride serving as solvent.

Suitable solvents for hydrogen peroxide or the peracid are also those which are inert under the reaction conditions, such as water, ether, benzene, or halogenated hydrocarbons, for example chloroform, dichloroethane, and chlorobenzene. The oxidation agent is generally used in an amount of from one to several molar equivalents, calculated on the starting compound of formula III′. Higher amounts may also be used without disadvantage. The reaction proceeds smoothly at a temperature in the range of from −50° C. to 150° C. In general, the reaction is carried out at room temperature or under cooling.

The starting compounds of formula III′ are obtained, for example, be reacting correspondingly substituted 2- or 4-hydroxypyridines or quinolines with (a) corresponding carbamoyl halides or (b) with phosgene or chloroformic acid esters with subsequent futher reaction with a suitable secondary amine (cf. German Offenlegungsschrift No. P 23 61 438). The compounds according to the invention have a considerably higher melting point than the starting compounds of formula III' and, therefore, can be readily separated therefrom, for example by recrystallization.

The compounds of formula I' have a very good selective insecticidal activity, especially against aphids, and furthermore possess excellent aystemic properties. They exert their activity not only via the plant foliage but also via the root system. Therefore, aphids living hidden inside of plant parts can be combated with good results. The compounds are likewise active against aphids which have become resistant to phosphoric acid esters.

Examples of aphids which can be combated successfully by the new compounds are *Breviceryme brassicae, Myzaphis rosarium, Aphis schneideri; Eriosomatidae* such as *Eriosoma lanigerum;* gall-forming aphids such as *Hemphigus* spec. as well as *Myzodes perisicae.*

On the other hand, useful coloepters (such as lady bugs), butterflies, orthopterae, dipterae, hymenopterae (such as ichneumon flies), and predactory mites feeding on insect pests are not affected even by high concentrations of the active ingredients. The action on aquatic organisms is insignificant, the componds having an action on fish only at high concentrations.

The compounds of the present invention or the preparations containing them may be applied in widely varied manners. They may be applied to the foilage and/or affected parts of it or, on the other hand, to the earth surrounding the plant.

Marketable compositions containing these compounds may be in the form of dusting formulations, powders or granules, wherein the active ingredient is present in admixture with solid extenders or carrier materials such as inert substances in powder or granular form. Generally, these compositions contain from 3–75% of these compounds. Suitable solid extenders or carrier materials are, for example, kaolin, bentonite, kieselguhr, dolomite, calcium carbonate, talcum, ground magnesia (chalk), fuller's earther, plaster, diatomaceous or agrillaceous earth. The compositions may also be used as wettable powders containing - in addition to the active ingredient - known wetting agents and/or dispersing agents and optionally fillers and/or emulsifiers as further additives.

The compositions may further be used as liquid preparations such as emulsion concentrates for spray liquors which normally contain the active ingredient together with one or several wetting agents, dispersion auxiliaries, or emulsifiers. For liquid preparations organic solvents may also be used. Before application these emulsion concentrates are normally further diluted to concentrations down to 0.005%.

The wettable, dispersion and emulsifying agents may be of either one of the cationic, anionic, or non-ionic type.

The compounds of formula I may also be used as active ingredients in fumigants.

The following examples further illustrate the invention.

EXAMPLES OF PREPARATION

EXAMPLE 71

2,6-Dimethyl-4-dimethylaminocarbonyloxy-pyridine- 1 oxide

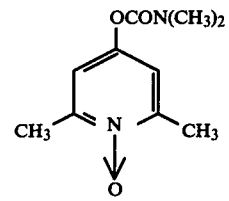

19.4 g (0.1 mole) of 2,6-dimethyl-4-dimethylaminocarbonyloxy-pyridine were dissolved in 150 ml of anhydrous chloroform free of alcohol and, while externally cooling with icewater and stirring, a solution of 25 g of 3-chloroperbenzoic acid (70% strength) in 400 ml chloroform was added dropwise.

After standing for 4 days at room temperature the chloroformic solution was shaken three times with 100 ml each of 2N soda solution and one time with distilled water and the aqueous extracts were discarded.

After drying of the chloroform phase over calcium chloride the chloroform was distilled off in vacuo at a bath temperature not exceeding 40° C. The oily residue was crystallized from n-hexane yielding 13.2 g of a product that still contained a small proportion of initial carbamate as ascertained by thin layer chromatography. The crude product was therefore recrystallized twice from acetonitrile, yielding 5.9 g of a product which was substantially free of initial carbamate and melted at 189°–190° C. (the initial carbamate melted at 75°–76° C.).

EXAMPLE 72

2-Methyl-4-dimethylaminocarbonyloxy-quinoline-1 oxide

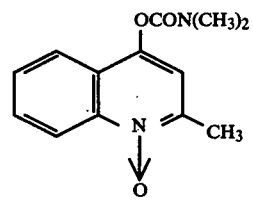

23 g (0.1 mole) of 2-methyl-4-dimethylaminocarbonyloxyquinoline were dissolved in 150 ml of dry chloroform free of alcohol and, while stirring and externally cooling with ice-water, 25 g 3-chloroperbenzoic acid (70% strength) dissolved in 400 ml chloroform were added dropwise.

After standing for 5 days at room temperature the chloroformic solution was shaken three times with 100 ml each of 2N soda solution and one time with 100 ml distilled water and the aqueous phases were discarded.

After drying over calcium chloride the chloroform was distilled of in a rotary evaporator. The crystalline residue which contained traces of initial carbamate was recrystallized from-n-hexane/toluene with addition of a small amount of charcoal. 14.5 g of pure crystalline N-oxide melting at 152° C. were obtained (the initial carbamate is liquid at room temperature)

EXAMPLE 73

2-Methyl-4-dimethylaminocarbonyloxy-5,6,7,8-tetrahydroquinoline-1 oxide

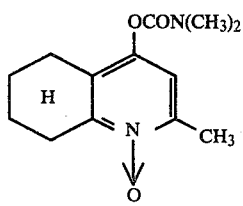

Under the conditions specified in Examples 1 and 2, 18 g (0.077 mole) of 2-methyl-4-dimethyl-5,6,7,8-tetrahydroquinoline were oxidized in chloroform with 13.5 g 3-chloroperbenzoic acid (70% strength).

After removal of chloroform and recrystallization of the residue from n-hexane/benzene, 9.5 g of pure N-oxide melting at 197°–198° C. were obtained (Melting point of initial carbamate 89°C.).

EXAMPLE 74

2-Methyl-6-methoxy-4-dimethylaminocerbonyloxyquinoline-1 oxide

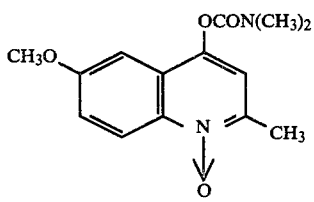

33.5 g (0.13 mole) of 2-methyl-6-methoxy-4-dimethylaminocarbonyloxyquinoline were dissolved in 280 ml glacial acetic acid and 30 ml of a 30% solution of hydrogen peroxide were added dropwise at about 0° to 8° C.

After standing for 40 days at room temperature, 2N soda solution was added with external cooling under the reaction mixture had a pH of 5. The separating crystals of the oxidation product were filtered off, washed with cold water and dried. 37 g of crude product were obtained which were freed from traces of initial carbamate by recrystallization, first from ethanol, then from acetonitrile and finally from benzene. 8 g of pure N-oxide melting at 172°–173° C. were finally obtained (melting point of initial carbamate 80°–81° C.).

EXAMPLE 75

2-Methyl-6-methoxy-4-dimethylaminocarbonyloxy-5,6,7,8-tetrahydroquinoline-1 oxide

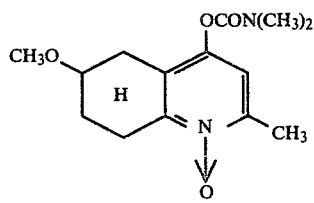

25.5 (0.096 mole) of 2-methyl-6-methoxy-4-dimethylaminocarbonyloxy-5,6,7,8-tetrahydroquinoline were dissolved in 75 ml dry, alcohol-free chloroform and oxidized as described in Examples 1 and 2 with a solution of 30 g 3-chloro-perbenzoic acid in 230 ml chloroform.

After working up under the conditions specified in the foregoing examples an oily crude product (31 g) was obtained from which 13 g of crystalline product were obtained by crystallization with n-hexane. The product was recrystallized from n-hexane/benzene yielding 6 g of uniform N-oxide melting at 121°–122° C., (melting point of the starting compound 49°—51° C.).

The following N-oxides of pyridine and quinoline carbamates were prepared in analogous manner:

| Ex. | structural formula | melting point |
|---|---|---|
| 76 | ![structure with C6H5O, OCON(CH3)2, CH3, N→O] | 141°–142° C. |
| 77 | ![structure with OCON(CH3)2, OCH3, CH3, N→O] | |
| 78 | ![structure with Cl, OCON(CH3)2, CH3, N→O] | 164°–166° C. |
| 79 | ![structure with CH3, OCON(CH3)2, CH3, CH3, N→O] | 165°–167° C. |
| 80 | ![structure with HCF2O, OCON(CH3)2, CH3, N→O] | |
| 81 | ![structure with OCON(CH3)2, OC6H5, CH3, N→O] | |
| 82 | ![structure with OCON(CH3)2, CH(CH3)2, CH3, N→O] | |

-continued

| Ex. | structural formula | melting point |
|---|---|---|
| 83 | 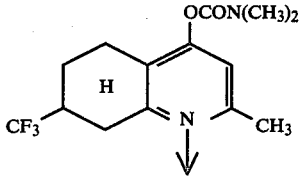 | 165° C. |
| 84 | 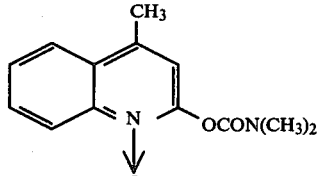 | 130°–131° C. |
| 85 | 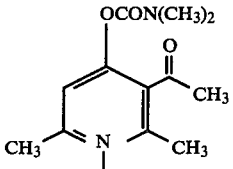 | 123°–124° C. |
| 86 | 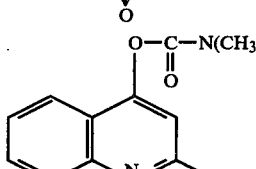 | 140°–150° C. |
| 87 | 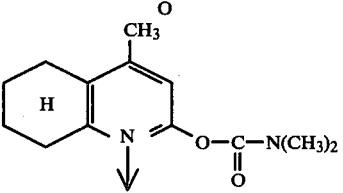 | 115°–122° C. |
| 88 | 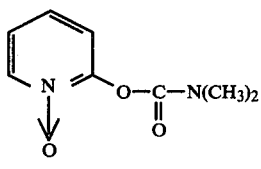 | 80°–84° C. |
| 89 | 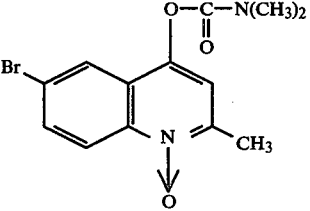 | 195° (decomposition) C. |

EXAMPLES OF FORMULATION

EXAMPLE C

A wettable powder readily dispersable in water is obtained by grinding 12 parts by weight of 2-methyl-4-dimethylaminocarbonyloxy-quinoline-1 oxide as active ingredient with
3 parts by weight of calcium-magnesium:aluminium silicate and mixing the product obtained with
45 parts by weight of a mixture prepared from
10 parts by weight of cellulose pitch (potassium salt of ligninsulfonic acid)
49 parts by weight of silica (quartz and kaolinite)
8 parts by weight of colloidal silicic acid
7 parts by weight of polypropylene oxide/colloidal silicic acid 1:1
1 part by weight of sodium oleylmethyl taurate.

EXAMPLE D

An emulsifiable concentrate consists of 1.5 parts by weight of 2-methyl-4-dimethylaminocarbonyloxy-5,6,7,8-tetrahydroquinoline-1 oxide
6.5 parts by weight of cyclohexane as solvent and
2.0 parts by weight of ethoxylated nonyl phenol as emulsifier

BIOLOGICAL EXAMPLES

EXAMPLE VII

Potted horse beans (*Vicia faba*) infested with a stabilized population of bean aphids (*Doralis fabae*) were sprayed to the drip off with an aqueous dilution of the emulsion concentrate containing the compound of Example 72 as active ingredient in decreasing concentrations. 3 days later the percentage of killed aphids was determined by counting the surviving and killed animals.

The result is indicated in the following Table I in comparison with two compunds of similar structure and comparable efficiency. The compounds of Example 71 to 76, 78, 80, and 83 to 89 had practically the same efficiency.

Table II

| Formula | % active compound per liter spray liquor | % mortality |
|---|---|---|
| 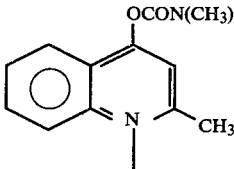 | 0.000375<br>0.00019<br>0.000095 | 100<br>75<br>40 |
| from Netherlands Spec. 6,606,695<br> | 0.006<br>0.003<br>0.0015<br>0.0006 | 100<br>98<br>60<br>20 |
| Isolan<br> | 0.005<br>0.0025<br>0.0012<br>0.0006 | 100<br>96<br>60<br>20 |

EXAMPLE VIII

The root systems of potted horse beans infested with a population of bean aphids (*Doralis fabae*) were wrapped in sheets and a glass funnel was inserted into the center of each system. By means of the glass funnels aqueous dilutions of an emulsion concentrate of the compound of Example 72 in decreasing concentration were uniformly distributed in the root area of the test plants. After 8 days the percentage of mortality was determined by counting the dead and surviving apaids on the plants. mg of active compound

| per root system | 0.5 | 0.25 | 0.125 | 0.06 |
|---|---|---|---|---|
| % mortality | 100 | 100 | 92 | 45 |

Practically the same results were obtained with the other compounds listed in Example VII.

EXAMPLE VIII

Populations of *Myzodes persicae* on potted paprika plants (*Capsicum anuum*) were sprayed to the drip off with aqueous dilutions of an emulsion concentrate containing the compound of Example 72 in decreasing concentrations. 2 days later the mortality rate was determined by counting the surviving and the dead animals.

| % active substance per liter spray liquor | 0.003 | 0.0015 | 0.00075 | 0.000375 |
|---|---|---|---|---|
| % mortality | 100 | 100 | 92 | 50 |

The results obtained with the other compounds listed in Example VII were practically identical.

We claim:

1. A compound having the formula

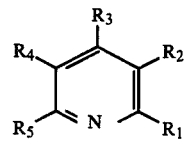

I wherein
one or $R_1$ and $R_3$ is

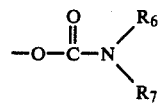

II and the other is hydrogen, $(C_1-C_3)$ alkyl or trifluoromethyl;
$R_2$ is hydrogen; $R_4$ and $R_5$ together are tetramethylene or —CH=CH—CH=CH—, which are unsubstituted or mono substituted by fluorine, $C_1-C_4$ alkyl, $C_1$ to $C_3$ alkoxy, or trifluoromethyl, and $R_6$ and $R_7$ are $CH_3$.

2. The compund of claim 1 which is

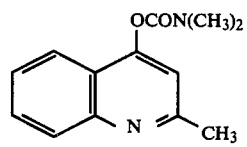

3. The compound of claim 1 which is

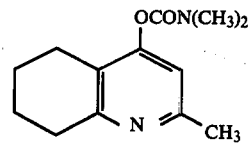

4. The compound of claim 1 which is

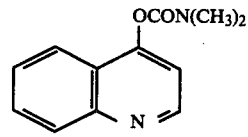

5. The compound of claim 1 which is

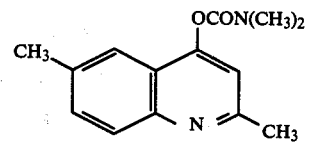

6. The compound of claim 1 which is

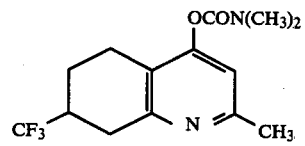

7. The compound of claim 1 which is

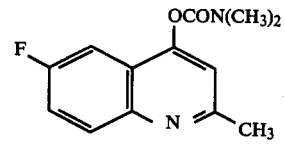

8. The compound of claim 1 which is

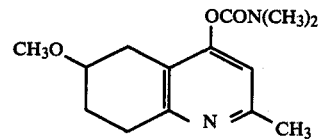

9. An aphicidal composition which comprises an aphicidally effective amount of a compound as claimed in claim 1 in combination with a carrier.

10. Method of combating aphids which comprises applying to the aphids or to the locus to be protected from aphids, an aphicidally effective amount of a compound as claimed in claim 1.

11. A compound having the formula

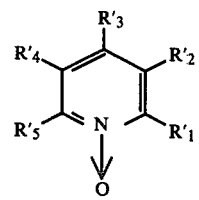

I' in which one of R'₁ and R'₃ is

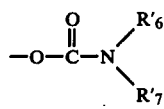

and the other is hydrogen, $C_1$ to $C_3$ alkyl or trifluoromethyl;

R'₂ is hydrogen;

R'₄ and R₅ together are tetramethylene or —CH=CH—CH=CH—, which are unsubstituted or mono substituted by halogen, $C_1$ to $C_4$ alkyl, $C_1$ to $C_3$ alkoxy, or trifluoromethyl; and R'₆ and R'₇ are CH₃.

12. The compound of claim 11 which is

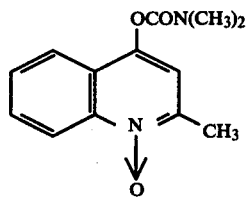

13. The compound of claim 11 which is

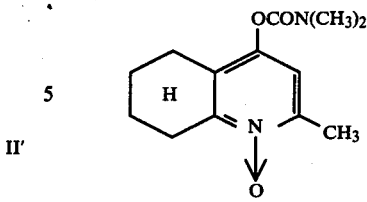

14. The compound of claim 11 which is

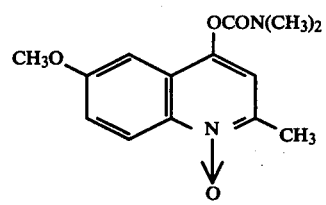

15. The compound of claim 11 which is

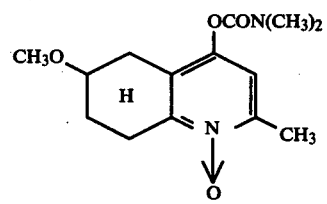

16. A composition for combating aphids containing an effective amount as active ingredient of a compound of claim 11 in combination with a carrier.

17. Method of combating aphids which comprises applying to the aphids or to the locus to be protected from aphids an aphicidally effective amount of a compound as claimed in claim 11.

* * * * *